United States Patent [19]

Ullman et al.

[11] Patent Number: 4,935,147

[45] Date of Patent: Jun. 19, 1990

[54] PARTICLE SEPARATION METHOD

[75] Inventors: Edwin F. Ullman, Atherton; Vartan E. Ghazarossian; Nurith Kurn, both of Palo Alto; Litai Weng, Mt. View, all of Calif.

[73] Assignee: Syntex (U.S.A.) Inc., Palo Alto, Calif.

[21] Appl. No.: 262,771

[22] Filed: Oct. 26, 1988

Related U.S. Application Data

[63] Continuation of Ser. No. 811,202, Dec. 20, 1985, abandoned.

[51] Int. Cl.$^5$ .......................... B01D 35/06; B03C 1/00
[52] U.S. Cl. .................................... 210/695; 210/222; 435/2; 435/261
[58] Field of Search .............. 210/222, 223, 695, 704, 210/705, 710; 435/2, 240.1, 261; 209/214

[56] References Cited

FOREIGN PATENT DOCUMENTS 2019378 10/1979 United Kingdom .

OTHER PUBLICATIONS

Widder et al., "Specific Cell Binding . . . ", J. Pharmaceutical Sciences, vol. 70, No. 4, Apr. 1981, pp. 387–389.
Mosbach, *Nature*, 270 (17) 259–261 (1977).

*Primary Examiner*—W. Gary Jones
*Attorney, Agent, or Firm*—Theodore J. Leitereg

[57] ABSTRACT

A method is disclosed for separating a substance from a liquid medium. The method comprises combining the liquid medium containing the substance with magnetic particles under conditions for non-specific chemical binding of the magnetic particles. Thereafter, the medium is subjected to a magnetic field gradient to separate the particles from the medium. The preferred non-specific binding is achieved as the result of charge interactions between the particles usually by means of a polyionic reagent. The method of the invention has particular application to the separation of cells and microorganisms from aqueous suspensions and also to the determination of an analyte in a sample suspected of containing the analyte. The analyte is a member of a specific binding pair (sbp). The sample is combined in an assay medium with magnetic particles and a sbp member complementary to the analyte. Magnetic or non-magnetic particles capable of specific binding to the analyte or its complementary sbp member must be included in the assay medium. The combination is made under conditions for non-specifically aggregating the magnetic particles or coaggregating the magnetic and non-magnetic particles when non-magnetic particles are present. The assay medium is subjected to a magnetic field gradient to separate the aggregated particles from the medium. Then, the medium or the particles are examined for the presence or amount of the analyte or an sbp member, the binding of which is affected by the presence of the analyte.

26 Claims, No Drawings

PARTICLE SEPARATION METHOD

This is a continuation of pending application Ser. No. 06/811,202, filed December 20, 1985, now abandoned, incorporated herein by reference.

BACKGROUND OF THE INVENTION

1. Field of the Invention

This invention relates to methods for separating a substance, usually particulates, from a fluid medium by use of a magnetic field gradient. The invention has particular application to separation of cells from biological fluids, such as blood, lymphatic fluid, urine, cell cultures, etc.

Numerous techniques are known for determining the presence or amount of an analyte in a sample, such as a biological fluid, for example, serum or urine. An in vitro assay procedure is the most common of these techniques. Many of these techniques involve competitive binding of the analyte to be determined and a labeled analog of such analyte to binding sites on a specific receptor, for example, an antibody. Many of these techniques involve a separation step where the unbound labeled analog is separated from bound labeled analog and either the bound or unbound analog is examined for the signal produced by the label. The signal is produced in relation to the amount of analyte in the sample.

Several techniques are known for separating bound and unbound fractions. For example, one may employ differential migration of the bound and the free fractions, e.g., chromatoelectrophereses, gel filtration, etc.; chemical precipitation of the bound or free fraction, e.g., by means of organic solvents, salts, acids, etc. followed by filtration or centrifugation; immunological precipitation of the bound fraction, e.g., by double antibody technique followed by filtration or centrifugation; absorption of the bound or free fraction onto selective sorbing media, e.g., charcoal, silicates, resins, etc.; magnetic separation techniques, and the like.

Magnetic separations generally fall into two general categories. There are those separations in which the material to be separated is intrinsically magnetic. On the other hand, one or more components of a mixture can be rendered magnetic by the attachment of a magnetically responsive entity. In biochemical separations, materials of interest are generally not sufficiently magnetic and thus magnetic particles bound to antibodies, lectins, and other targeting molecules have been used for isolating many of these materials. Magnetic particles targeted for specific molecules have also been used in a variety of immunoassays.

Many of the separation techniques used in immunoassays are relatively long and complicated procedures. Such procedures reduce operator efficiency, decrease thoughput, and increase the costs of tests. Other separation techniques which are rapid and simple do not adequately distinguish between the bound and free fractions and therefore are unsuited for immunoassays or can only be utilized in a limited number of tests.

2. Description of the Related Art.

A method for determining the concentration of substances in biological fluids (e.g., drugs, hormones, vitamins and enzymes) wherein magnetically responsive, permeable, solid, water insoluble, micro particles are employed is disclosed in U.S. Pat. No. 4,115,534. Functional magnetic particles formed by dissolving a mucopolysaccaride such as chitosan in acidified aqueous solution containing a mixture of ferrous chloride and ferric chloride is disclosed in U.S. Pat. No. 4,285,819. The microspheres may be employed to remove dissolved ions from waste aqueous streams by formation of chelates. U.S. Pat. No. 3,933,997 describes a solid phase radio immunoassay for digoxin where anti-digoxin antibodies are coupled to magnetically responsive particles. Small magnetic particles coated with an antibody layer are used in U.S. Pat. No. 3,970,518 to provide large and widely distributed surface area for sorting out and separating select organisms and cells from populations thereof. U.S. Pat. No. 4,018,886 discloses small magnetic particles used to provide large and widely distributed surface area for separating a select protein from a solution to enable detection thereof. The particles are coated with a protein that will interact specifically with the select protein. U.S. Pat. No. 4,070,246 describes compositions comprising stable, water insoluble coatings on substrates to which biologically active proteins can be covalently coupled so that the resulting product has the biological properties of the protein and the mechanical properties of the substrate, for example, magnetic properties of a metal support. A diagnostic method employing a mixture of normally separable protein-coated particles is discussed in U.S. Pat. No. 4,115,535. Microspheres of acrolein homopolymers and copolymer with hydrophilic comonomers such as methacrylic acid and/or hydroxyethylmethacrylate are discussed in U.S. Pat. No. 4,413,070. U.S. Pat. No. 4,452,773 discloses magnetic iron-dextran microspheres which can be covalently bonded to antibodies, enzymes and other biological molecules and used to label and separate cells and other biological particles and molecules by means of a magnetic field. Coated magnetizeable microparticles, reversible suspensions thereof, and processes relating thereto are disclosed in U.S. Pat. No. 4,454,234. A method of separating cationic from anionic beads in mixed resin beds employing a ferromagnetic material intricately incorporated with each of the ionic beads is described in U.S. Pat. No. 4,523,996. A magnetic separation method utilizing a colloid of magnetic particles is discussed in U.S. Pat. No. 4,526,681. UK Patent Application GB No. 2,152,664A discloses magnetic assay reagents.

An electron-dense antibody conjugate made by the covalent bonding of an iron-dextran particle to an antibody molecule is reported by Dutton, et al. (1979) *Proc. Natl. Acad. Sci.* 76:3392–3396. Ithakissios, et al. describes the use of protein containing magnetic microparticles in radioassays in *Clin. Chem.* 23:2072–2079 (1977). The separation of cells labeled with immunospecific iron dextran microspheres using high gradient magnetic chromotography is disclosed by Molday, et al. (1984) *FEBS* 170:232–238. In *J. Immunol. Meth.* 52:353–367 (1982) Molday, et al. describe an immuno specific ferromagnetic iron-dextran reagent for the labeling and magnetic separation of cells. An application of magnetic microspheres in labeling and separation of cells is also disclosed by Molday, et al. in *Nature* 268:437–438 (1977). A solid phase fluoroimmunoassay of human albumin and biological fluids is discussed by Nargessi, et al. (1978) *Clin. Chim. Acta.* 89:455–460. Nye, et al. (1976) *Clin. Chim. Acta.* 69:387–396 discloses a solid phase magnetic particle radioimmunoassay. Magnetic fluids are described by Rosenweig (1983) *Scien. Amer.* 10:136–194. Magnetic protein A microspheres and their use in a method for cell separation are disclosed by Widder, et al. (1979) *Clin. Immunol. and Immunopath.* 14:395-400.

SUMMARY OF THE INVENTION

The method of the present invention is directed to the separation of a substance from a liquid medium by causing the binding of the substance to very small magnetic particles. Where the substance is present as a non-particulate solute, it will normally bind to the magnetic particles through specific ligand-receptor binding. Where the substance is present as non-magnetic particles, binding may also be specific but will usually be non-specific such as through electrostatic or hydrophobic interactions. Chemical means is then provided to non-specifically bind the magnetic particles to each other and usually to the non magnetic particles and to cause aggregation or coaggregation of the particles. Next the medium is subjected to a magnetic field gradient to separate the particles from the medium. Preferably the non specific binding is achieved through charge interactions and is reversible.

The method of the present invention has particular application in the assay of organic and biochemical analytes particularly those analytes of interest in the analysis of body fluids. Of special interest are assays where the analyte is a member of a specific binding pair (sbp) that is bound, or can become bound, to the surface of a particle. Where the analyte is a surface component or becomes bound to a non-magnetic particle, the method involves combining in an assay medium the sample, the non-magnetic particle when the analyte becomes bound to such particle, and magnetic particles under conditions for binding non-magnetic and magnetic particles and chemically inducing non-specific agglutination of the magnetic particles. The non-magnetic particle or the magnetic particle is usually bound to an sbp member. If the sbp member on the non-magnetic particle is not complementary to the analyte, then a complementary sbp member is also added. Next, the assay medium is subjected to a magnetic field gradient to separate the particles from the medium. After the separation, the medium or the particles are examined for the presence or amount of an sbp member, which is affected by the presence of analyte in the sample. Normally, the sbp member is detected by virtue of a signal created by the use of a signal producing system that generates a signal in relation to the amount of the analyte in the sample. The particles separated from the medium can be washed prior to their examination. Furthermore, the particles can subsequently be treated after separation from the medium to reverse their non-specific binding.

The method of the invention provides a way of separating non-magnetic particles from a medium by virtue of the chemically controlled non-specific reversible binding of such particles to magnetic particles. Because of the small size of the magnetic particles, it also provides for very rapid binding of a substance to be separated. By then aggregating the particles there is provided a much more rapid and complete magnetic separation than has been achieved by previous methods.

The invention includes compositions and kits for conducting the method of the invention, particularly for conducting an assay for determining an analyte in a sample suspected of containing the analyte.

DESCRIPTION OF THE SPECIFIC EMBODIMENTS

The present invention relates to a method of separating substances bound to suspended particles from a liquid medium. The method involves magnetic particles and chemically controlled non-specific binding of the magnetic particles to each other. Usually the substance to be separated will be bound to, or will be caused to bind to, non-magnetic particles. The preferred approach for achieving non-specific binding between the non-magnetic particles and the magnetic particles or between the magnetic particles themselves is charge interactions. The bound particles are separated from the medium by the use of a magnetic field gradient. The separated particles can be washed and examined by physical or chemical methods. The particles can also be treated to reverse the non-specific binding. Where non-magnetic particles are used, reversal of binding can be followed by separation of the free magnetic particles to provide a means of separating the non-magnetic particles from the magnetic particles.

The present method has wide application in the field of the separation of suspended particles from a medium, particularly for separating biological materials, such as cells and microorganisms, and in the fields of immunoassays and blood typing. The invention provides a separation method which is more convenient and rapid than centrifugation, filtration, and prior magnetic separation methods and is particularly applicable to the pretreatment of suspensions where it is desired to carry out an analysis of either the particle-free liquid medium or the separated particles. The invention also has application to the assay of an analyte in a sample where a separation step is required.

Before proceeding further with the description of the specific embodiments of the present invention, a number of terms will be defined.

Analyte—the compound or composition to be measured, the material of interest. The analyte can be a member of a specific binding pair (sbp) and may be a ligand, which is mono- or polyvalent, usually antigenic or haptenic, and is a single compound or plurality of compounds which share at least one common epitopic or determinant site. The analyte can also be a component of a particle or can become bound to a particle during an assay. Exemplary of an analyte that is a component of a particle is an antigen on the surface of a cell such as a blood group antigen (A, B, AB, O, D, etc.) or an HLA antigen. Exemplary of an analyte becoming bound to a particle during an assay is an sbp member where a complementary sbp member is bound to a particle, glycoprotein or glycolipids where a lectin is bound to a particle, antibodies where protein A is bound to a particle, and the like. The binding involved when an analyte becomes bound to a particle can be specific or non-specific, immunological or non-immunological.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

The precise nature of some of the analytes together with numerous examples thereof are disclosed in U.S. Pat. No. 4,299,916 to Litman, et al., particularly at columns 16 to 23, the disclosure of which is incorporated herein by reference.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight, among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chloropromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Ligand analog or analyte analog—a modified ligand or ligand surrogate or modified analyte or analyte surrogate which can compete with the analogous ligand or analyte for a receptor, the modification providing means to join a ligand analog or analyte analog to another molecule. The ligand analog or analyte analog will usually differ from the ligand or analyte by more than replacement of a hydrogen with a bond which links the ligand analog or analyte analog to a hub or label, but need not. The term ligand surrogate or analyte surrogate refers to a compound having the capability of specifically binding a receptor complementary to the ligand or analyte. Thus, the ligand surrogate or analyte surrogate can bind to the receptor in a manner similar to the ligand or analyte. The surrogate could be, for example, an antibody directed against the idiotype of an antibody to the ligand or analyte.

Poly(ligand analog)—a plurality of ligand analogs joined together covalently, normally to a hub nucleus. The hub nucleus is a polyfunctional material, normally polymeric, usually having a plurality of functional groups, e.g., hydroxyl, amino, mercapto, ethylenic, etc. as sites for linking. The hub nucleus may be water soluble or insoluble, preferably water soluble, and will normally be at least about 30,000 molecular weight and may be 10 million or more molecular weight. Illustrative hub nuclei include polysaccharides, polypeptides (including proteins), nucleic acids, anion exchange resins, and the like. Water insoluble hub nuclei can also include walls of containers, e.g. glass or plastic, glass beads, addition and condensation polymers, Sephadex and Agarose beads and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the invention.

Ligand-any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Non-magnetic particles—diamagnetic or paramagnetic particles usually with a magnetic susceptibility (X) of less than $1\times10^{-5}$ emu/Oecm$^3$. The non-magnetic particles are generally at least about 0.02 microns and not more than about 100 microns, usually at least about 0.05 microns and less than about 20 microns, preferably from about 0.3 to 10 microns diameter. The non-magnetic particle may be organic or inorganic, swellable or non-swellable, porous or non-porous, preferably of a density approximating water, generally from about 0.7 to about 1.5 g/ml, and composed of material that can be transparent, partially transparent, or opaque. Usually the non-magnetic particles will have a charge, either positive or negative, and may have sbp members on their surface. Normally, the non-magnetic particles will be biologic materials such as cells and microorganisms, e.g., erythrocytes, leukocytes, lymphocytes, hybridomas, streptococcus, staphylococcus aureus, E. coli, viruses, and the like. The non-magnetic particles can also be particles comprised of organic and inorganic polymers, liposomes, latex particles, phospholipid vesicles, chylomicrons, lipoproteins, and the like.

The polymers will normally be either addition or condensation polymers. Non-magnetic particles derived therefrom will be readily dispersible in the assay medium and may be adsorptive or functionalizable so as to bind, either directly or indirectly, an sbp member or a magnetic particle.

Frequently, the non-magnetic particles will be an analyte, be bound to an analyte, or will become bound to an analyte during an assay. The non-magnetic particles not initially bound to the analyte can be derived from naturally occurring materials, naturally occurring materials which are synthetically modified and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The non-magnetic particles for use in assays will usually be polyfunctional and will have bound to or be capable of specific non-covalent binding to an sbp member, such as antibodies, avidin, biotin, lectins, protein A, and the like. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, *J. Biol. Chem.*, 245 3059 (1970). The length of a linking group may vary widely, depending upon the nature of the compound being linked, the effect of the distance between the compound being linked and the particle on the binding of sbp members and the analyte and the like.

The non-magnetic particle will normally have an electronic charge, either positive or negative. The particle can be inherently charged or can be treated chemically or physically to introduce a charge. For example, groups such as carboxyl, sulfonate, phosphate, amino, and the like can be chemically bound to or formed on the particles by techniques known in the art. Cells are normally negatively charged due to the presence of sialic acid residues on the cell surface. Latex particles can be positively or negatively charged but normally will have a negative charge as a result of the introduction of functional groups or absorption of charged polymers such as polypeptides, proteins, polyacrylate, and the like.

The non-magnetic particles can be fluorescent or non-fluorescent, usually non-fluorescent, but when fluorescent can be either fluorescent directly or by virtue of fluorescent compounds or fluorescers bound to the particle in conventional ways. The fluorescers will usually be dissolved in or bound covalently or non-covalently to the non-magnetic particle and will frequently be substantially uniformly bound through the particle. Fluoresceinated latex particles are taught in U.S. Pat. No. 3,853,987 and are available commercially as Covaspheres from Covalent Technology Corp.

The fluorescers of interest will generally emit light at a wavelength above 350 nm, usually above 400 nm and preferably above 450 nm. Desirably, the fluorescers have a high quantum efficiency, a large Stokes shift and are chemically stable under the conditions of their conjugation and use. The term fluorescer is intended to include substances that emit light upon activation by electromagnetic radiation or chemical activation and includes fluorescent and phosphorescent substances, scintillators, and chemiluminescent substances.

Fluorescers of interest fall into a variety of categories having certain primary functionalities. These primary functionalities include 1- and 2-aminonaphthalene, p,p-diaminostilbenes, pyrenes, quaternary phenanthridine salts, 9-aminoacridines, p,p'-diaminostilbenes, imines, anthracenes, oxacarbocyanine, merocyanine, 3-aminoequilenin, perylene, bis-benzoxazole, bis-p-oxazolyl benzene, 1,2-benzophenazine, retinol, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates oxides and salts. Exemplary fluorescers are enumerated in U.S. Pat. No. 4,318,707, columns 7 and 8, the disclosure of which is incorporated herein by reference. Squaraine dyes described in U.S. patent application Ser. No. 773,401, filed September 6, 1985 (the relevant disclosure of which is incorporated by reference) are also useful as fluorescers.

Additionally, light absorbent non-magnetic particles can be employed which are solid insoluble particles of at least about 10 nm in diameter.

Many different types of particles may be employed. Of particular interest are carbon particles, such as charcoal, lamp black, graphite, colloidal carbon and the like. Besides carbon particles metal sols may also find use, particularly of the noble metals, gold, silver, and platinum.

Label—A member of the signal producing system that is conjugated to an sbp member. The label can be isotopic or non-isotopic, usually non-isotopic, including catalysts such as an enzyme, a chromogen such as a fluorescer, dye or chemiluminescer, a radioactive substance, a particle, and so forth.

Signal Producing System—The signal producing system may have one or more components, at least one component being a label. The signal producing system generates a signal that relates to the presence or amount of analyte in a sample. The signal producing system includes all of the reagents required to produce a measurable signal. When the label is not conjugated to an sbp member analogous to the analyte, the label is normally bound to an sbp member complementary to an sbp member that is analogous to the analyte. Other components of the signal producing system can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by measurement of the degree of aggregation of particles or by use of electromagnetic radiation, desirably by visual examination. For the most part, the signal producing system will involve particles, such as fluorescent particles or other light absorbing particles, a chromophoric substrate and enzyme, where chromophoric substrates are enzymatically converted to dyes which absorb light in the ultraviolet or visible region, phosphors, fluorescers or chemiluminescers.

The signal-producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of analyte in the sample.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and β-galactosidase. Alternatively, luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

Magnetic particles—particles that are intrinsically magnetically responsive or have been rendered magnetic by, for example, attachment to a magnetically responsive substance or by incorporation of such substance into the particles. The magnetic particles can be paramagnetic, ferromagnetic, or superparamagnetic, usually paramagnetic and will have magnetic susceptibilities (X) of at least $5 \times 10^{-5}$ emu/Oecm$^3$, usually at least $4 \times 10^{-4}$ emu/Oecm$^3$. The diameter of the particles should be small, generally in the range from about 5 nm to 1 micron, preferably from about 10 to 250 nm, more preferably from about 20 to 100 nm, most preferably colloidal.

Exemplary of the magnetic component of particles that are intrinsically magnetic or magnetically responsive are complex salts and oxides, borides, and sulfides of iron, cobalt, nickel and rare earth elements having high magnetic susceptibility, e.g. hematite, ferrite. The magnetic component of other such particles includes pure metals or alloys comprising one or more of these elements.

For the most part the magnetic particles will contain a core of the magnetic component with surface functional groups such as hydroxyl, silicate, carboxylate, sulfate, amino, phosphate and the like. Frequently, an additional surface coating will be employed that is covalently or non-covalently bound to the surface. The surface coating can be an anionic or cationic detergent, usually anionic; or the coating can be a protein such as albumin, immunoglobulin, avidin, fetuin or the like; or it can be a carbohydrate such as dextran, chitosan, amylose and the like, or combinations or these substances in their native form or functionalized so as to control their charge and hydrophilicity. Alternatively, the particles can be coated with other amphiphilic substances such as lipopolysaccharides, octyl glucoside, etc.

Alternatively, the magnetic component can be incorporated into a particle such as, for example, impregnating the substance in a polymeric matrix. However, this procedure frequently gives particles larger than the magnetic particles of this invention. For a more in-depth discussion of the preparation of magnetic particles by this method, see Whitesides, et al. (1983) *Trends in Biotechnology,* 1(5):144–148 and references cited therein.

Preferred magnetic particles of less than a hundred nanometers in diameter can be made by precipitating iron oxides in the presence or absence of a coating such as a polysaccharide or protein. Magnetic particles of a few microns diameter can also be made by a ball milling process and removing material which is not in the size range of interest. Typically, magnetic particles formed by this latter process are quite polydisperse, and not as generally useful. More useful monodisperse metal oxide suspensions can be prepared by careful control of pH, temperature and concentrations during the precipitaion process. Coating the magnetic particles with macromolecules can increase their colloidal stability. This can be done by direct adsorption of high molecular weight polymers or by functionalizing the surface of the particle and then binding macromolecules to the functional groups. Emulsion polymerization and grafting techniques provide a means for coating magnetic particles with polymers.

In general, the magnetic particle that is best for a given task will be determined primarily by the size and properties of the particles to be separated. For immunoassays or the isolation of cells, the magnetic particles preferably should be readily suspendable, form stable, preferably colloidal, suspensions, and have high magnetic susceptibility. Where an sbp member is bound to the surface, its ability to bind to a complementary sbp should be retained and should be stable with time.

Small (<100 nm) magnetic particles are advantageously used in immunoassays and cell separation procedures. These particles preferably have a homogenous core of metal, metal oxide or other metal compound. When colloidally stable, small particles can be suspended for long periods of time. Their large surface to volume ratio and relatively higher rates of diffusion enable them to quickly bind molecules and particles that are dispersed in the medium. Small magnetic particles are also less susceptible than large magnetic particles to aggregation due to residual magnetic moments after they have been exposed to a large applied magnetic field. Also, methods are known for colloidally stabilizing such small particles.

Magnetic particles of an intermediate size (100-1000 nm) can also be employed. They can be suspended readily and require a lower surface charge density to prevent spontaneous aggregation than do smaller particles. Magnetic particles of this size range can be created by emulsion polymerization and have the advantage of a surface that is easily modified whether by grafting or the covalent bonding of macromolecules to their surface. However, they remain suspended for shorter times and their lower surface to volume ratio decreases the rate of binding to the substance to be separated.

Magnetic fluid—a colloidal suspension of magnetic particles in a liquid carrier that are not readily separated by a magnetic field. The resulting liquid has the bulk properties of a magnetic material. The fluid becomes spontaneously magnetized in the presence of an external magnetic field. The liquid also acts as a fluid and is capable of assuming the shape of its container, of flowing, and of moving around obstacles. Exemplary of a magnetic fluid is a ferrofluid where the suspended particles are ferromagnetic particles (see, for example, Rosenweig, supra, and U.S. Pat. No. 4,019,994, the disclosure of which is incorporated herein by reference, and Khalafolla, et al. (1980) *IEEE Transactions on Magnetics*, MAG-16:178–183).

The colloidal magnetic particles can be coated with protein material, e.g., a serum protein such as albumin, gammaglobulin, etc., and the like. The colloidal magnetic particles can be mixed with an aqueous buffered solution of protein to prepare the protein-coated colloidal magnetic particles. The coating of the magnetic particles with protein can be accomplished by physical (e.g., absorption) or chemical binding.

Non-specific binding—non-covalent hinding between particles that is relatively independent of specific surface structures. Such non-specific binding will usually result from charge or electronic interactions between oppositely charged particles or between particles having the same charge where a polyionic reagent having a charge opposite thereto is employed. Non-specific binding may also result from hydrophobic interactions between particles.

Polyionic reagent—a compound, composition, or material, either inorganic or organic, naturally occurring or synthetic, having at least two of the same charge, either polyanionic or polycationic, preferably at least ten of the same charge; e.g., a polyelectrolyte.

Exemplary of polycationic reagents are polyalkylene amines such as polyethyleneimine and polypropyleneimine and their lower alkyl ammonium salts such as polybrene $(-N(CH_3)_2CH_2CH_2N(CH_3)_2CH_2CH_2CH_2CH_2-)_n$, metal ions such as calcium and barium ion, aminodextrans, protamine, positively charged liposomes, polylysine, and the like.

Exemplary of polyanionic reagents are heparin, dextran sulfate, negatively charged phospholipid vesicles, polycarboxylic acids, such as polyacrylate, polyglutamate and the like. The above materials and their preparation or isolation are well known in the art and many are commercially available.

Releasing agent—a compound, composition, or material, either naturally occurring or synthetic, organic or inorganic, capable of reversing the non-specific binding between particles, i.e., dissociating such particles. The releasing agent acts upon the non-specific bond between the particles. For example, where the non-specific binding results from charge interactions, the releasing agent can act to change the pH of the medium to one which is unfavorable or incompatible with the charge interactions. The releasing agent can, therefore, be an acid such as a mineral acid or an organic acid or a base such as a mineral base or an organic base. Alternatively, the releasing agent can act to shield ionic interactions and thus can be a high ionic strength solution or a solution of a neutral polymer such as dextran. Alternatively, the releasing agent can have a charge which disrupts the non-specific binding between the particles and the magnetic particles. Exemplary of the latter are be polyelectrolyte salts such as citrate, polyacrylate, dextran sulfate, and the like. Where the particles are bound by a polyionic bridge, the releasing agent can be a polyionic agent of opposite charge or can be a reagent which depolymerizes the polyionic reagent. Where the particles and magnetic particles are of opposite charge, other positively or negatively charged polyelectrolytes or high ionic strength solutions may be used.

Ancillary Materials-Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

As mentioned above, the present invention involves a method for separating a substance from a liquid medium. The method comprises combining a liquid medium containing the substance with magnetic particles, preferably dispersed as a magnetic liquid, under conditions for binding the substance to the magnetic particles and non-specifically binding and aggregating the magnetic particles where a chemical means is used to cause the suspended magnetic particles to non-specifically bind to one another. The substance to be separated will frequently be a non-magnetic particle or will be bound to a non-magnetic particle. The non-specific binding is usually conveniently obtained as the result of charge interactions, which can also serve to non-specifically bind non magnetic particles to the magnetic particles. For example, the non-magnetic particles and the magnetic particles can have opposite electronic charges and non-specific binding will occur spontaneously. Where the particles and the magnetic particles have the same charge, a polyionic reagent having an opposite charge can be added to the medium to cause non-specific binding between the non-magnetic particles and the magnetic particles and between the magnetic particles. After the above combination is formed, the medium is subjected to a magnetic field gradient to separate the particles from the medium.

In carrying out the method, a liquid, usually aqueous, medium will be employed. Other polar solvents may also be employed, usually oxygenated organic solvents from one to six, more usually from one to four, carbon atoms, including alcohols, ethers, and the like. Usually these cosolvents will be present in less than about 40 weight percent, more usually in less than about 20 weight percent. The pH for the medium will usually be selected to promote non-specific binding and aggregation of the magnetic particles prior to separation. Where the particles are negatively charged, increasing the pH will tend to increase the charge and prevent spontaneous aggregation caused by non-specific hydrophobic and Van der Waals interactions. The converse applies to positively charge particles. Where an oppositely charged polyelectrolyte is added to cause aggregation, changes in pH that increase the charge of the polyelectrolyte will often decrease the charge of the particles and an optimum pH must be selected that will avoid the use of excessive amounts of this reagent. Generally, a pH range of 5 to 10, more usually 6 to 9, will be used. For assays, other considerations with respect to pH are to maintain a significant level of binding of sbp members while optimizing signal producing proficiency. In some instances, a compromise will be made between these considerations. Various buffers may be used to achieve the desired pH and maintain the pH during the determination. Illustrative buffers include borate, phosphate, carbonate, Tris, barbital, and the like. The particular buffer employed is not critical to this invention; however, in individual separations or individual assays, one buffer may be preferred over another. When non-magnetic particles are involved, a reagent that promotes reversal of the binding of the particles and the magnetic particles can be added after the separation has been accomplished.

Moderate temperatures are normally employed for carrying out the method and usually constant temperatures during the period for conducting the method. Generally, the temperatures will be chosen to promote non-specific binding of the particles prior to separation. The temperature for the method, particularly involving an assay, will generally range from about 0° to 50° C., more usually from about 15° to 40° C. Again, after separation is accomplished a temperature that promotes reversal of the binding of the particles and the magnetic particles can then be chosen.

The concentration of the magnetic particles in the medium will depend on the amount of the substance in the medium that is to be separated and whether or not it is particulate, the rate of separation that is desired, the magnetic field gradient and field strength, the magnetic susceptability of the magnetic particles and the like. In general, higher concentrations of magnetic particles provide more efficient and rapid separations but too high a concentration can cause excessive entrainment of the medium. The concentration is normally determined empirically and will generally vary from about 0.1 to 1000 $\mu$g/ml, more usually from about 0.5 to 200 $\mu$g/ml, frequently from about 1 to 50 $\mu$g/ml.

Where non-magnetic particles are to be separated from a medium, the concentration of the non-magnetic particles can vary widely depending upon the need. For example, in separation of cells from blood, the cell volume may represent 50% of the total volume of the blood. By contrast, it may be desired to separate as few as 1000 bacteria/ml from a sample of water. When it is necessary to obtain non-magnetic particles that are relatively free of the medium as in an assay, usually the total volume of the non-magnetic particles should be less than 5% of the medium. In an assay where the analyte is a component of a particle or becomes bound to a particle, the analyte will generally vary from about $10^{-4}$ to $10^{-14}$M, more usually from about $10^{-6}$ to $10^{-12}$M. Where non-magnetic particles other than natural particles associated with the analyte are added to the medium, their concentration will depend on numerous factors such as particle size and surface area, concentration of the analyte, desired rate of reaction with the analyte or complementary sbp and the like. In general, added non-magnetic concentrations will be about 0.01 to 100 $\mu$g/ml, more usually from about 0.1 to 20 $\mu$g/ml. Considerations such as the concentration of the analyte, non-specific binding effects, desired rate of the reaction, temperature, solubility, viscosity, and the like will normally determine the concentration of other assay reagents.

While the concentrations of the various reagents will generally be determined by the concentration range of interest of the particles to be separated or of the concentration range of the analyte in an assay, the final concentration of each of the reagents will normally be determined empirically to optimize the rate and extent of separation of the particles and, in the case of an assay, the sensitivity and specificity of the assay over the range of interest.

Chemical means for forming non-specific bonds between the particles will usually be included in the liquid medium. Except where non-magnetic particles are to be separated that have an opposite charge to the magnetic particles, this chemical means is usually a polyionic reagent having a charge opposite to that of the particles. The amount of polyionic reagent added should be sufficient so that substantially all of the particles become aggregated or coaggregated. This concentration must be determined empirically. Excess reagent must generally be avoided because this interferes with complete aggregation of the particles. Generally, the polyionic reagent will have a concentration in the liquid medium sufficient to provide a number of ions associated with the polymer and equal to the total number of charges of opposite sign on all the particles in the medium. Where non-magnetic particles are to be separated that have an opposite charge to the magnetic particles, the chemical means for forming non-specific bonds between the particles will frequently be a low ionic strength buffer.

In an assay, the aqueous medium can also contain one or more members of a single producing system. As mentioned above the concentration of the various members of the single producing system will vary and be dependent upon the concentration range of interest of the analyte and the type of measurement or assay involved. As a general point, the concentration of the various members of the signal producing system will be selected to optimize the signal produced in relation to the concentration range of interest of the analyte.

The binding of non-magnetic particles to magnetic particles or of magnetic particles to each other is affected by pH. The binding is also affected by other factors such as ionic strength and the presence of ionic and non-ionic polymers. Generally, where non-specific binding is due to charge interactions the ionic strength should be chosen initially to facilitate the binding between the particles. For this purpose the ionic strength is generally low and can be in the range of 0.001 to 0.5M, preferably 0.005 to 0.1M. After the separation has been completed, the ionic strength can be adjusted upward to facilitate the reversal of the coupling of the particles and the magnetic particles. For this purpose, the ionic strength of the medium will normally be from about 0.1 to 3M, preferably from about 0.15 to 1M. The principles for causing particles to aggregate or to remain suspended are well known in the field of colloid science.

After the magnetic particles have been combined in the liquid medium for the purpose of an assay where specific binding to the magnetic particles is required, the liquid medium is then held for a period of time sufficient for the binding to occur. Normally this requires 0.5–120 minutes, more frequently 1–60 min. The subsequent chemically induced non-specific aggregation of the magnetic particles, and the non-specific coaggreation of particles when only non-specific binding of particles is required, will occur essentially instantaneously, and it is usually sufficient to allow the mixture to stand for 60 sec., frequently less than 15 sec.; preferably the magnetic field is applied immediately after mixing. The extent of binding between the particles and the magnetic particles or between magnetic particles controls the efficiency of the magnetic separation.

After aggregation of the particles, a magnetic field is applied to achieve a separation of the particles from the medium. The application of a magnetic field to the medium can be carried out in a conventional manner that provides for a high magnetic field gradient. Normally, the method is conducted in a container made of non-magnetic material, for example, glass or plastic. In applying the magnetic field, the reaction container can be placed in close proximity to an electromagnet or permanent magnet, preferably permanent, which has a geometry to maximize the field intensity and gradient within the suspension. The higher the strength of the magnetic field and the higher the gradient, the faster the separation. Normally, it will be convenient to carry out the separation in a tube of diameter from about 2 to 50 mm, preferably from about 3 to 15 mm, with one or more permanent magnets mounted as close to the tube as practical to provide field strengths of at least about 200 Oe and preferably at least about 1KOe with magnetic field gradients usually at least about 20 KOe/cm. The magnetic field is applied for a sufficient period of time to provide the desired degree of separation of the particles from the medium. Depending on the geometry, field strength, magnetic susceptibility of the particle and the like, the magnetic field is applied for a period of about 2 seconds to 1 hour, preferably about 5 seconds to 60 seconds.

Once the particles have been concentrated to one part of the container, the suspending liquid medium can be separated from the particles by any convenient means such as, for example, decantation, pipeting, and the like.

The particles separated from the liquid medium can be treated to reverse the non-specific binding between the particles by suspending the particles in a liquid medium with reagents added to facilitate reversal of the binding. In one approach, where the particles are bound by ionic interactions, ionic strength and the pH of the medium can be adjusted to facilitate reversal of the binding. Generally, increasing the ionic strength will reverse electrostatic binding. Where the particles are negatively charged, a decrease in pH will lower the charge and reduce binding interactions. Alternatively, if a polycationic aggregating agent is used, increasing the pH can neutralize the charge and reverse binding. Thus, it may be desirable to change the pH to as high or low value as allowed by the stability of the reagents, usually no less than pH 4 or greater than pH 10.

The reversal of the binding between the particles and the magnetic particles is dependent upon the nature of the non-specific binding between the particles. Where non-specific binding results from charge interaction, an agent can be added to reverse the charge interactions responsible for the non-specific binding. For example, a releasing agent can be added. Where binding results from aggregation of particles with opposite charges, either a polycationic or polyanionic polyelectrolyte can be used. Where the particles have like charges and an oppositely charged polyelectrolyte was the chemical means for binding the particles, a polyelectrolyte of the same charge as on the particles can be used to dissociate the particles. The polyelectrolytes can be, for example, polyanions such as dextran sulfate, heparin, polyglutamate, polyacrylate, phospholipid vesicles, carboxymethyedextran. Aminodextran, chitosan, polybrene, polyethyleneimine, and cationic liposomes are exemplary of polycations that can be employed.

Where a polycation was used to initiate non-specific binding between the particles and the magnetic particles, or between the magnetic particles, a polyanion can be employed to reverse the binding. Alternatively, where a polyanion was used to form the non-specific binding between the particles and the magnetic particles or between the magnetic particles, a polycation can be used to reverse the binding. For example, where polycations such as polybrene or barium ion have been employed, the releasing agent can be a polyanion such as citrate or sulfate. Detergents can act as a releasing agent for liposomes and when particles are non specifically aggregated primarily through hydrophobic interactions.

The concentration of the releasing agent should be sufficient to result in substantial or complete reversal of the non-specific binding between the particles. The concentration of the releasing agent is generally dependent upon the nature of binding between the particles and the magnetic particles and the nature of the particles. Generally, the concentration of the releasing agent will be at least equal to the concentration of ionic or hydrophobic sites on the particles, preferably at least 10 fold higher.

It is important to choose the releasing agent with regard to the nature of the particles in the aggregate so as to minimize or avoid damage to the particles after the release from the aggregate.

Once the particles have been separated from the aggregate, they may be used as desired. For example, in an assay the separated particles can be examined for the presence of a detectable signal in relation to the amount of an analyte in the sample. The separated particles can be cells which can be used as desired. For example, the separated particles can be red blood cells.

In a preferred embodiment of the invention, the magnetic particles are provided as a magnetic liquid, e.g., ferrofluid. The particles to be separated are combined with the magnetic liquid.

An important application of the present method is the removal of cells from a sample containing cells such as, for example, removal of red blood cells from whole blood. In the method, using whole blood by way of example and not by way of limitation, a whole blood sample is combined in a liquid medium with charged magnetic particles under conditions for non-specific binding of the magnetic particles to the cells. The cells will usually have a negative charge by virtue of sialic acid residues or the like on the surface of the cells. The magnetic particles can be positively charged, resulting in direct non-specific binding between the cells and the magnetic particles. Preferably, the magnetic particles have a negative charge. In this latter instance a polycationic reagent is included in the medium to provide conditions for non-specific binding between the cells and the magnetic particles. Useful polycationic reagents in this method can be, for example, polybrene, polyalkyleneimines, aminodextran, chitosan, and positively charged liposomes. The preferred polycationic reagent for removing cells from whole blood is polybrene or polyethyleneimine.

Next, the medium can be subjected to a magnetic field gradient to separate the cells from the medium. Application of the magnetic field results in concentration of the cell-magnetic particle aggregate to one portion of the container, which permits its removal of the residual cell-free medium by, for example, decantation, pipetting, etc.

The separated cell-magnetic particle aggregate can then be treated to release the cells from the aggregate as described above. Where polybrene or polyethyleneimine is employed as a polycationic binding agent, preferred releasing agents are citrate or polyacrylate.

The present method provides particluar advantages for automated blood typing procedures by providing a way to prepare blood plasma without centrifugation. It is also useful in the Coombs antiglobulin test where immunoglobulin-containing plasma is first combined with test cells and must then be fully removed in order to determine if antibodies from the plasma have bound to the cells. In this procedure magnetic particles and a non-specific binding agent are added to the mixture of plasma and test cells and the subsequent separated cells are resuspended with the help of a releasing agent. Moreover, the present method can be employed in immunoassays wherein an spb member is bound to a particle and it is desired to separate and wash the particles without centrifugation; the particles can be magnetic or non-magnetic.

The present invention has application to assays for an analyte in a sample suspected of containing the analyte. The analyte is an spb member. In the assay the sample is combined in an assay medium with an spb member complementary to the analyte wherein at least one of the analyte or the complementary spb member is associated with the surface of a non-magnetic particle, usually a cell, latex particle, or a magnetic particle. The present invention offers the improvement of combining charged magnetic particles with the medium under conditions for non-specific binding and aggregation of the magnetic particles. Frequently, the conditions for non-specific binding include combining a polyionic reagent to cause non-specific binding between the magnetic particles. The assay will normally involve a signal producing system for producing a detectable signal in relation to the amount of analyte in the sample. The signal producing system usually includes a labeled sbp member. The medium may be further combined with none, one or more members of the signal producing system. The medium is subjected to a magnetic field gradient to separate aggregates comprising the magnetic particles from the medium. The separated aggregates or the medium can be examined for the presence of a detectable signal. Such a determination can require the addition of any remaining members of the signal producing system not added above. The separated aggregates can be treated according to the above conditions to separate non-magnetic particles from the magnetic particles prior to examining for the presence of a detectable signal. After the non-magnetic particles have been separated from the magnetic particles, the non magnetic particles may be examined for the presence of a detectable signal produced in relation to the amount of analyte in the sample. For this purpose they can be combined with any remaining members of the signal producing system not added above in order to generate a detectable signal.

The invention further comprises a composition comprising an aggregate of (a) non-magnetic particles to which are bound an sbp member and that are non-specifically electrostatically bound to (b) magnetic particles. The composition may further comprise a polyionic reagent of opposite charge to the magnetic particles and the non-magnetic particles when the non-magnetic particles and magnetic particles have the same charge. The aggregate of the composition is generally capable of being disassociated into its component particles by employing a releasing agent. Alternatively, the composition of the invention can comprise magnetic particles to which are bound an sbp member and a polyionic reagent wherein the magnetic particles are non-specifically bound to one another.

As a matter of convenience, the reagents for conducting an assay can be provided in a kit in package combination in predetermined amounts for use in assaying for an analyte. The kit can comprise (a) an sbp member complementary to the analyte, (b) an sbp member bound to a charged particle if neither the analyte nor the complementary sbp member is bound to a charged particle and (c) charged magnetic particles where the particles are not magnetic. The kit can also include reagents for generating a signal in relation to the amount of analyte in the sample. Furthermore, the kit can comprise a polyionic reagent having a charge opposite to that of the particles when all the particles have the same charge. Additionally, the kit can further comprise a releasing agent for reversing the binding between the particles. Ancillary agents can be included as necessary.

EXAMPLES

The invention is described further by the following illustrative examples. All parts and percentages herein are by volume unless otherwise indicated. Temperatures are in degrees Centigrade (°C.).

EXAMPLE 1

Preparation of Plasma

Uncoagulated whole blood (480 μl, 16 mg/ml) and a ferrofluid (250 μl, 4.5 mg Fe/ml) were sequentially added to a container placed in a magnetic field produced by a permanent magnet. The magnitude of the magnetic field was 4.0 Kgauss. The erythrocyte-particle aggregates moved towards the magnet poles and greater than 99% of erythrocytes present in blood were removed. The clear plasma was transferred to another container by decantation. Results were obtained on blood from 175 subjects; the time for complete separation varied from 15–85 sec. The ferrofluid comprised iron magnetic particles coated with succinylated bovine serum albumin. The ferrofluid was prepared according to Example 4. The succinylated bovine serum albumin was prepared as described in Example 4.

EXAMPLE 2

Assay for Anti-Rh Antibody

To the plasma prepared in Example 1 were added polyacrylic acid (10 μl, 2 mg/ml) and Rh positive test cells stained with a squarate dye. Fifty μl squarate dye ($10^{-4}$M, dissolved in DMF) was added to a suspension of 1 ml of erythrocytes. (The squarate dye was 2-(p-dibutyl-amino-m-hydroxyphenyl)-4-(4-diethylimmonio-2-hydroxy-2,5-cyclohexadienylidene)-3-oxo-1-cyclobutenolate and was prepared by condensing squaric acid with 3-N,N-dibutyl-aminophenol in n-butanol:toluene (2:1) followed by azeotropic removal of water.) The mixture was incubated for 8 min. at 37° C. Buffer (16 gm/l glycine, 0.03M NaCl, 0.015M phosphate pH 6.7) (500 μl), ferrofluid, and polybrene (10 μl, 16 mg/ml) were then sequentially added and separation of test cells occurred in the presence of a magnetic field having the same intensity as described above. The test cells (held via the aggregation in accordance with the present invention against the sides of the container) were washed twice with buffer (a low ionic strength saline solution, phosphate (0.003M), pH 6.7 containing 0.24M glycine and 0.03M NaCl). Next polyacrylic acid (10 μl, 2 mg/ml) followed by antihuman immunoglobulin containing 1% polyvinylpyrrolidone (PVP) were added. After a 3 min. incubation at 25° C., the reaction mixture was diluted with citric acid (800 μl, 0.2M) and analyzed by a fiber optic particle cytometer method described by Briggs, J., et al, *J. Immunol.* 81, 73–81 (1985) and in U.S. patent application Ser. No. 397,285 filed July 12, 1982, the disclosure of which is incorporated herein by reference in its entirety.

Briefly, in U.S. Ser. No. 397,285, method and apparatus are provided for determining the presence of particles in a dispersion in relation to the detection of the presence or amount of a material of interest. An optical fiber is used to define a relatively small volume from which fluorescent light can be received and analyzed. The volume is related to the volume in which there is likely to be only a single particle that results in a predetermined fluctuation. By employing a variety of techniques that allow for changes in fluorescence fluctuations in relation to the presence of an analyte in a sample, the amount of analyte present may be determined. The fluctuations are observed over a period of time in a static mode or by sampling a plurality of volumes in the sample. By comparing the observed results with results obtained with assay solutions having a known amount of analyte, the amount of analyte can be quantitatively determined.

The results from the above experiment are summarized in the following table:

TABLE 1

| Sample | Signal[a] |
|---|---|
| Control plasma | 30 ± 4 |
| Control plasma spiked with anti-Rh Ab[b] | 80 ± 9 |

[a] A signal greater than 5 SD (standard deviation) from control plasma was regarded as positive.
[b] Enough anti-Rh antibody was added to give a 1+ score (scale 1+ to 4+) with a commercially available antibody screen test using conventional anti-human serum.

The results demonstrate that a sensitive assay for anti-Rh antibody can be carried out in accordance with the present invention.

EXAMPLE 3

Separation of Beads Labeled with Anti-triiodothyronine (T3)

A. Reagents and Abbreviations

1. PB-T3($^{125}$I) = carboxysubstituted polystyrene beads labeled with anti-T3 antibodies (radioiodinated) by EDAC coupling.

2. MP = magnetic particles a) PGA = magnetite derivatized with glucuronic acid through phosphate (0.2–0.8 μm). b) CM-Dex$_3$ ("ferrofluid") = carboxymethyl dextran - magnetite (0.030–0.45 μm) prepared according to a procedure similar to that described in U.S. Pat. No. 4,452,773. c) M4100 BioMag-COOH (0.2–1.0 μm) M4100 BioMag particles from Advanced Magnetics Inc.; succinylated on free amine groups of particles.

3. Polybrene = Hexadimethrine Bromide obtained from Sigma Chem. Co.

4. Assay buffer = PBS/0.1% BSA.

5. Normal human serum.

B. Procedure

To 250 μl of PB-T3($^{125}$I), containing 55 μg bead, was added 50 μl Assay Buffer or normal human serum. After incubating this mixture for 20 minutes at room temperature, 100 l of MP was added (PGA, CM-Dex$_m$ or BioMag-COOH) containing 0.2 mg Fe. To this reaction mixture, 50 μl of polybrene (at varying concentration) was added. After agitating for about 3 minutes, the tubes were placed in a magnetic field having an intensity of 2.6 Kgauss for five minutes. After separation, the supernates were decanted and the pellets counted using Beckman gamma 5500 counter.

C. Results

TABLE 2

| Magnetic Particles Used | Concentration of Polybrene (mg/ml) | | Amount of Polystyrene Removed from Reaction Mixture (%) | |
|---|---|---|---|---|
| | buffer | serum | buffer | serum |
| PGA | 0.14 | 0.56 | 92 | 73 |
| CM-Dex$_m$ | 0.4 | 0.4 | 87 | 84 |
| Biomag-COOH | 0.035 | 0.14 | 88 | 77 |

Removal of 0.26 μm polystyrene beads, coated with anti-T$_3$ antibodies, from reaction mixture by coaggregating them with negatively charged magnetic particles using polybrene.

TABLE 3

| Magnetic Particles Used | Concentration of Polybrene (mg/ml) | | Amount of Polystyrene Removed from Reaction Mixture (%) | |
|---|---|---|---|---|
| | buffer | serum | buffer | serum |
| PGA | 0.035 | 0.14 | >99 | >99 |
| CM-Dex$_m$ | 0.4 | 0.4 | >99 | >99 |
| BioMag-COOH | 0.035 | 0.14 | >99 | >99 |

Removal of 0.51–1.2 micrometer polystyrene beads, coated with anti-T$_3$ antibodies, from reaction mixture, by coaggregating them with negatively charged magnetic particles using polybrene.

TABLE 4

| Magnetic Particles Used | Concentration of Polybrene (mg/ml) | | Amount of Polystyrene Removed from Reaction Mixture (%) | |
|---|---|---|---|---|
| | buffer | assay | buffer | serum |
| PGA | 0.035 | 0.14 | 92 | 92 |
| CM-Dex$_m$ | 0.4 | 0.4 | 98 | 98 |
| BioMag-COOH | 0.035 | 0.14 | 90 | 94 |

Removal of succinylated 0.26 μm polystyrene beads, coated with anti-T$_3$ antibodies, from reaction mixture, by coaggregating them with negatively charged magnetic particles using polybrene.

TABLE 5

| NaCl (moles/l) | CPM$^a$ removed from Reaction (%) | |
|---|---|---|
| | PGA | CM-Dex$_3$ |
| 0 | 95 | 82 |
| 0.058 | 93 | 80 |
| 0.086 | 90 | 88 |
| 0.141 | 94 | 90 |
| 0.252 | 88 | 32 |
| 0.474 | 5 | 4 |

CPM = counts per minute

TABLE 6

| Polybrene (mg/ml) | CPM removed from reaction (%) | |
|---|---|---|
| | PGA | CM-Dex$_3$ |
| 0 | 19 | 2 |
| 0.025 | 20 | 2 |
| 0.07 | 90 | 3 |
| 0.14 | 94 | 5 |
| 0.28 | 93 | 55 |
| 0.56 | 90 | 90 |
| 1.12 | 88 | 92 |
| 2.24 | 85 | 93 |
| 4.48 | 87 | 91 |
| 8.96 | 90 | 82 |
| 17.92 | 56 | 16 |

Discussion

We have demonstrated that polystyrene beads coated with anti-T$_3$ antibodies can be effectively removed from a reaction mixture by coaggregating them nonspecifically with negatively charged magnetic particles, using polybrene and a magnetic field.

The results presented in Tables 2, 3, and 4 indicate that larger polystyrene beads can be removed from the reaction mixture more effectively than small beads. Also, the difference of removal efficiency between succinylated and nonsuccinylated polystyrene beads indicates that the charge distribution on the surface of microparticles contributes to the coaggregation and hence to the removal efficiency.

The results showing the effect of ionic strength and polystyrene concentration on the separation of polystyrene beads is presented in Tables 5 and 6. At high NaCl concentrations, the coaggregation of particles, and hence the removal of the polystyrene beads, was substantially reduced. This demonstrates that coaggregation was based on interactions between negatively and positively charged groups. Table 6 shows that there is an optimum concentration of polybrene and too high or two low concentrations have reduced ability to cause aggregation.

It was demonstrated that the polystyrene beads coated with anti-T3 antibodies can be effectively removed from the reaction mixture within one minute (including aggregation time and magnetic separation time).

The present method can be an attractive approach for removing a bound fraction from a reaction mixture in heterogenous immunoassays where, e.g., microbeads, labeled with antibodies or antigens, are employed.

EXAMPLE 4

Preparation of Ferrofluid

A. Preparation of Colloidal Magnetic Iron Oxide (Ferrofluid)

A solution of 20 ml 2M FeCl$_3$, 10 ml 2M FeCl$_2$, and 20 ml 1M HCl was added dropwise over five minutes with stirring to a solution of 25 ml concentrated NH$_4$OH in 500 ml water. The precipitate settled out, and the supernatant was decanted. The residue was stirred for two minutes with 500 ml 2M HClO$_4$ and again allowed to settle out. The supernatant was decanted, and the residue was taken up in water and dialyzed against 10 mM HClO$_4$. The resulting colloid had a volume of 80 ml and an iron content of 28 mg/ml. The average particle size as determined by dynamic light scatter was 60 nm. Literature reference—R. Massart, *C. R. Acad. Sci. Paris*, 291*C*, 1 (1980).

B. Coating of Colloidal Magnetic Iron Oxide with Proteins

Rabbit Serum Albumin (RSA): A solution (2 ml) of 11 mg/ml RSA was added to 2 ml of a 1:4 dilution into water of the colloidal magnetic iron oxide from above. After five minutes, 0.50 ml of 550 mM Tris-HCl, pH 8.0, was added. The resulting colloid had no visible particulate matter.

Succinylated Bovine Serum Albumin (sBSA): A solution of 105 ml of 9.5 mg/ml sBSA (prepared by treatment of 5.0 g BSA in 250 ml 0.1M sodium phosphate, pH 8.0 with 0.20 g succinic anhydride) in water was adjusted to pH 3.38 with 0.1M HClO$_4$. A solution of 30 ml of 35 mg/ml colloidal magnetic iron oxide in 10 mM HClO$_4$ was diluted with 75 ml water and added to the sBSA solution. The pH of the solution was then adjusted to pH 9.06 with 1M NMe$_4$OH. The average particle size in the resulting colloid was determined by dynamic light scatter to be 63 nm.

EXAMPLE 5

Coagglutination of Ferrofluid and Latex Beads

Into a series of test tubes was pipetted 100 μl DC$_{16}$AS (1,3-bis[4-(dihexadecylamino)]-2,4-dihydroxycyclobutene diylium dihydroxide, bis (inner salt) dyed carboxylic latex beads (OD 0.455 μ. est. about 1.5×10$^8$ beads/ml, prepared as described in Example 7, Part A) in PBS buffer, 700 μl diluted freon-treated normal human serum (2.5% in PBS), and 100 μl of freshly diluted commercial, aqueous based ferrofluid EMG 805 200 g (Ferrofluidics Corp., Nashua, NH; 10% in PBS, the iron content was determined as ≈17 mg/ml). One hundred μl of 0.5% polybrene in PBS containing 0.011M β-CD (β-cyclodextran) was then added on vortex. Immediately, the test tube was placed into a Corning magnetic separator with a magnetic field intensity of 2.6 Kgauss. At different separation times, 500 μl aliquots of the separated liquid was then taken from a test tube, diluted with an equal volume of PBS buffer and the fluorescence measured as described in Example 2. As a control, total fluorescence was determined, using no magnetic particle and was found to be 60420 KH$_z$. The results are summarized in Table 7.

TABLE 7

| Separation Time (sec) | Fluorescence (KHz) | % |
|---|---|---|
| 60 | 526 | 0.87 |
| 30 | 727 | 1.2 |
| 20 | 933 | 1.5 |
| 10 | 1197 | 2.0 |
| 0 | 60420 | 100.0 |

The results indicated that the rate of polybrene coagglutination in accordance with the present invention is greater than 99% in 1 minute.

EXAMPLE 6

Effect of Concentration of Latex Beads on Coagglutination of Ferrofluid and Latex Beads A similar protocol as in Example 5 was used. Various concentrations of latex bead suspensions were prepared about ($10^7$ to $10^{10}$ beads/ml). A hundred μl of each stock suspension was taken into a test tube. To each test tube was then added 700 μl diluted serum (2.5% in PBS) and 100 μl diluted ferrofluid. After addition of 100 μl of 0.5% polybrene in PBS containing 0.011M β-CD, the mixture was vortexed ($\approx 3$ sec) and preincubated to a total of 10 seconds before inserting into the magnetic separator. At exactly 1 minute after polybrene addition (magnetic separation time 50 sec), 500 μl aliquot of the separated liquid was taken out, diluted to 1 ml, and fluorescence was determined. The controls used no magnetic particles and were diluted to proper concentration before measurement.

The results are summarized in Table 8.

TABLE 8

| Bead Stock (beads/ml) | Fluorescence Total | Remaining | (%) |
|---|---|---|---|
| $1.2 \times 10^{10}$ | $3.41 \times 10^5$ | 33060 | (0.97) |
| $6.3 \times 10^9$ | $1.86 \times 10^5$ | 18516 | (1.0) |
| $1.2 \times 10^9$ | $5.43 \times 10^4$ | 5218 | (0.96) |
| $7.9 \times 10^8$ | $2.71 \times 10^4$ | 1713 | (0.63) |
| $1.6 \times 10^8$ | $5.89 \times 10^3$ | 732 | (1.2) |
| $7.9 \times 10^7$ | $3.21 \times 10^3$ | 509 | (1.6) |
| $1.0 \times 10^7$ | $4.60 \times 10^2$ | 361 | (7.8) |

The above example demonstrates that up to $10^{10}$ beads/ml concentration of latex beads can be efficiently removed in less than 1 minute in accordance with the present invention.

EXAMPLE 7

Assay for Hepatitis B Surface Antigen (HBsAg)

Before describing the assay a number of terms will be defined:
RT—room temperature
EDAC—1-ethyl-3-(3-Dimethylaminopropyl)carbodiimide
PBS—phosphate buffered saline
DTE—dithiothrietol
EDTA—ethylenediaminetetraacetate, sodium salt
BSA—bovine serum albumin
IgM—immunoglobulin M
IgG—immunoglobulin G
NHS—N-hydroxysuccinimide
MP—magnetic particles
LISS—glycine 18 g/liter, potassium phosphate 230 mg/liter, sodium phosphate
squaraine dye—DC$_{16}$AS A. Preparation of squaraine dyed latex beads Carboxylated polystyrene particles (beads) of uniform 0.716 micron diameter were purchased from Duke Scientific Corp. of Palo Alto. The particles are manufactured by Dow Chemical Co. and are packaged in 15 ml vials containing 10% by weight of suspended solids in deionized water with trace amounts of nonionic surfactants.

The beads were prepared for dyeing by centrifugation (15,000 rpm for 10 min) and decantation of the supernatant fluid. The pellet was resuspended in ethylene glycol to the same volume as before centrifugation.

The squaraine dye was prepared by condensing squaric acid with dihexadecylphenyl amine (2:1 molar ratio) in refluxing n-butanol-benzene with azeotropic removal of water.

Five hundred micrograms of squaraine dye was dissolved in 0.5 ml hot benzyl alcohol in a small tube or vial (with magnetic stir bar) clamped in an oil bath maintained at 140°. The dye solution was slowly diluted with 1 ml ethylene glycol.

One milliliter of the ethylene glycol bead suspension was added dropwise to the hot dye solution while stirring vigorously. Stirring was continued for 15 minutes; then the mixture was pipetted into 5 to 10 ml of 70% ethanol in water. The dyed beads were centrifuged and washed twice in 70% ethanol and then sonicated to disperse the beads after centrifugation. The beads were washed twice in deionized water and then stored in deionized water at a concentration not exceeding 100 mg solids per ml.

B. Attachment of antibody to squaraine dyed latex beads via avidin biotin interaction:

1. Covalent attachment of avidin to squaraine latex beads.

Squaraine dyed latex beads (0.85 ml, $2.3 \times 10^{11}$ beads/ml, 0.716 μm diameter) were suspended in 2 ml dist. water and the carboxyl groups were activated by reaction with EDAC (sigma, 18.75 mg added to the bead suspension) for 3 to 4 min. at room temperature. The activated beads were then added to avidin D solution (Vector, 1.5 mg in 3 ml 0.1M NaCl) and the reaction was carried out over night at room temperature with occasional sonication. The beads were washed by centrifugation and coated with BSA by suspension in buffer (0.17M glycine, 0.1M NaCl, pH 9.2) containing 1% BSA (Sigma, RIA grade). The beads were washed by centrifugation, following incubation at room temperature for 1 hour, and resuspended in the same buffer without BSA (3 ml).

Biotin binding capacity was determined with $^{14}$C-biotin and was shown to be 77 pmol per $6 \times 10^8$ beads.

2. Preparation of biotinylated anti-HBsAg monoclonal antibody:

Anti-HBsAg monoclonal antibody IgG1 (from Celtek or Royal Free Hospital, purified by protein-A affinity chromatography, 1.0 mg/ml in 0.1M phosphate buffer, pH 8.2) was reacted with 25 fold molar excess biotinyl-NHS (Sigma, 3.4 mg/ml in DMF) for 4 hours at room temperature.

3. Immobilization of biotinylated antibody on avidin squaraine latex beads:

Biotinylated anti-HBsAg monoclonal anitbody (0.4 mg, 0.1M phosphated buffer, pH 8.2) was incubated with avidin latex beads ($1.25 \times 10^{10}$ beads) for 2 hours at room temperature. The beads were washed by centrifugation and resuspended in 0.01M glycine, 0.01M NaCl pH 8.2, 0.2% BSA. 0.05% Tween 20 (final bead concentration $6.25 \times 10^9$/ml).

C. Preparation of succinylated magnetic particles:

Two hundred (200) mg magnetic particles (Advanced Magnetic, BioMag 4100, 4 ml) were washed by magnetic separation ($3 \times 40$ ml 0.1M phosphate buffer, pH 7.0) and resuspended in 15 ml of the above buffer. The particles were reacted with succinic anhydride (5 ml of 1M in DMF) by addition of 5 aliquots over 2 hours (the pH was adjusted to 7.0 following each addition). The succinylated particles were washed by magnetic separation ($3 \times 40$ ml 0.1M phosphate buffer, pH 7.0, and $2 \times 40$ ml LISS), resuspended in 20 ml LISS and stored at 4° C. with 0.02% azide.

F. Assay Protocol:

Reagents:

1. Anti-HBsAg IgG1 monoclonal antibody (from Celtek or Royal Free Hospital, London) covalently attached to squarate dyed-latex beads (0.716µ diameter, preparation detailed above) (squaraine-latex beads-anti-HBsAg).

2. HBsAg (Abbott positive control, ASUZYME II, 6 ng/ml).

3. Magnetic particles: Succ-BioMag (100 mg/ml) prepared as described above.

4. Polybrene (Sigma, av. MW 5000) 10 mg/ml in LISS.

5. 0.2M citrate, pH 8.2.

6. IgM anti-HBsAg monoclonal antibody (Celtek) 0.5–1.0 mg/ml in 2X PBS.

G. Assay Procedure:

1. Squaraine-latex beads-anti HBsAg (5 µl containing $3 \times 10^7$ beads) was added to 100 µl sample [50% serum in LISS, with or without antigen (1.5 or 3 ng/ml)] and incubated for 8 min at RT.

2. Coaggreation of latex beads with magnetic particles was achieved by addition of 10 µl of succ. BioMag followed by 10 µl of polybrene.

3. Magnetic separation of latex-MP coaggregates was achieved in a magnetic field gradient of 2.3 Kgauss (1 min). The results are found below in Table 9.

4. Dissociation of the latex-MP coaggregates was achieved in 50 µl citrate.

5. Addition of IgM anti-HBsAg (5 µg) and incubation for 5 min at RT for antigen dependent agglutination.

6. Magnetic separation of succ. BiogMag from latex beads

7. Dilution with 0.2M citrate, pH 8.2 and measurement of squaraine latex agglutination by laser light scattering (Nicomp HN5-90). The results are set forth below in Table 10.

H. Results

1. Efficiency of separation of anti-HBsAg-squaraine latex beads from 50% serum:

The amount of anti-HBsAg-squaraine latex beads remaining in the serum following magnetic separation was assessed by fluorescence spectrophotometry.

TABLE 9

| Fluorescence of supernate | |
|---|---|
| With HBsAg (1.5 ng/ml in serum) | Without HBsAg |
| 3.0 | 3.9 |
| 3.0 | 3.0 |
| 2.2 | 5.7 |
| 5.8 | 1.9 |

(Total fluorescence units of anti-HBsAg-squaraine dyed latex beads assay: 98)

The above results demonstrate that an effective separation of dyed latex beads from the medium was achieved in accordance with the present invention.

2. The results of the assay for HBsAg are summarized in the following table:

TABLE 10

| Average Diameter (nm) | |
|---|---|
| With HBsAg (1.5 ng/ml in serum) | Without HBsAg |
| 2770 | 881 |
| 2760 | 795 |

The above results indicate that a sensitive assay for HBsAg can be carried out utilizing a separation in accordance with the present invention. A substantially higher level of agglutination was observed when the HBsAg was present in the medium.

EXAMPLE 8

Assay for Thyroid Stimulating Hormone

A. Abbreviations and some materials:

TSH—thyroid stimulating hormone, human
MP—magnetic particles
FF—ferrofluid from Ferrofluidics Corporation (EMG 805 200 g)
LC—long chain
11C6 or 9D7—monoclonal antibody to the α-subunit of hTSH
% B—% $^{125}$I-TSH bound (specific bound)
% NSB—% non-specific bound
BMP—Biomag particles from Advanced Magnetics Inc.
Buffer A—PBS +0.1% BSA +0.05% Tween 20, pH 7.4
PB—polybrene
r.t.—room temperature
Ab—antibody
Ag—antigin
Serum—TSH free serum from Immuno-search Inc.

B. Binding OF $^{125}$I-TSH to FF-avidin

One hundred (100) µl FF-avidin, prepared by adsorption of avidin on FF, and 100 µl biotin-LC-11C6 in Buffer A ($\approx 1$ µg antibody), and 100 µl $^{125}$I-TSH ($\approx 1$ ng/ml) in Buffer A or serum were incubated at r.t., 15 min. (buffer) or 25 min. (serum).

Fifty (50) µl of polybrene in PBS was added; in buffer, PB=1.6 mg/ml, held for 1 min.; in serum, PB=25 mg/ml, held for 3 min.

The material was subjected to a magnetic field of 2.1–2.6 Kgauss in a Corning magnetic separator for 3 min. The material was washed 1 time with 0.5 ml PBS +0.05% Tween 20, and the MP were counted. The results are summarized in Table 11.

TABLE 11

| MP | % B in buffer | % B in serum |
|---|---|---|
| FF-avidin | 51(1)* | 60(1)* |
| FF-avidin | 50(5)* | 65(1)* |
| BMP-avidin (control) | N.D.** | 68(2)* |

*% NSB in parenthesis
**N.D.-not determined

The above results indicate that ferrofluids coated with avidin can be separated in accordance with the present invention by combining with biotin bound to antibody and adding polybrene to non-specifically agglutinated the particles.

C. Binding of $^{125}$I-TSH to FF with addition of avidin

Fifty (50) μl avidin (2 μg), 100 μl $^{125}$I-TSH in buffer A or TSH free serum, and 100 μl biotin-LC-11C6 in buffer A were incubated at r.t. for 15 min.

Fifty (50) μl ferrofluid (containing ≈200 μl Fe) was added followed by 50 μl polybrene; for the assay in buffer: 1.6 mg/ml, for the assay in serum: 12.5 mg/ml.

The material was subjected to magnetic field of 2.1–2.8 Kgauss in a Corning magnetic separator for 3 min., washed 1 time, and counted. The results are summarized in Table 12.

TABLE 12

| particles | % B in buffer | % B in serum |
|---|---|---|
| FF | 53(10)* | 48(3)* |
| FF-avidin (control**) | 51(11)* | 49(2)* |
| BMP-avidin (control**) | 42(35)* | 52(4)* |

*% NSB in parenthesis
**In accordance with Section B above

The above results indicate that ferrofluids can be separated in accordance with the present invention by combining with avidin and biotin bound to antibody and adding polybrene to non-specifically agglutinated the particles.

D. Competitive TSH assay with FF-avidin

Fifty (50) μl TSH at 0, 200 ng, 2 μg, 20 g and 200 g/ml in serum (i.e. 0, 10 ng, 100 ng, 1 μg and 10 g/assay), 50 μl $^{125}$I-TSH (2 ng/ml, 0.1 ng/assay) in serum, 100 μl biotin-LC-9D7 (1 g Ab/assay) in buffer A, and FF-avidin prepared as described above were combined and incubated at r.t. for 15 min. Fifty (50) μl polybrene at 12.5 mg/ml was was added. After 3 min. the material was subjected to a magnetic field of 2.1–2.6 Kgauss, separated, washed and counted as above.

The results are summarized in Table 13.

TABLE 13

| TSH (ng/assay) | % B |
|---|---|
| 0 | 49 |
| 10 | 49 |
| 100 | 48 |
| 1000 | 21 |
| 10000 | 3.3 |

The above results indicate that an assay for TSH can be carried out utilizing a separation in accordance with the present invention. A substantially lower percent of binding was observed when TSH was present in the medium.

E. Competitive TSH assay with FF and addition of avidin

Fifty (50) μl TSH at 0, 200 ng, 2 g, 20 g and 200 g/ml in serum (i.e. 0, 10 ng, 100 ng, 1 g and 10 g/assay), 50 l $^{125}$I-TSH (2 ng/ml, 0.1 ng/assay) in serum, 100 μl biotin-LC-9D7 (1 g Ab/assay) in buffer A, and 50 μl avidin (2 g/assay) were incubated at r.t. for 15 min. Then, 50 μl FF (containing 200 g Fe) was added and after 5 min. 50 μl polybrene at 12.5 mg/ml was added. After 3 min. the material was subjected to a magnetic field of 2.1–2.6 Kgauss separated, washed and counted as above.

The results are summarized in Table 14.

TABLE 14

| TSH (ng/assay) | % B |
|---|---|
| 0 | 46 |
| 10 | 46 |
| 100 | 42 |
| 1000 | 20 |
| 10000 | 2.5 |

The above results indicate that an assay for TSH can be carried out utilizing a separation in accordance with the present invention. A substantially lower percent of binding was observed when TSH was present in the medium.

Although the foregoing invention has been described in some detail by way of illustration and example for purposes of clarity and understanding, it will be obvious that certain changes or modifications may be practiced within the scope of the appended claims.

What is claimed is:

1. In a method for separating suspended charged non-magnetic particles from a liquid medium, said method involving (a) coupling said charged non-magnetic particles to like-charged magnetic particles, and (b) separating the coupled particles from said medium by means of a magnetic field gradient, the improvement which comprises non-specifically coupling said charged non-magnetic particles to said like-charged magnetic particles by inclusion in said medium of chemical means for non-specifically coupling said charged non-magnetic particles to said like-charged magnetic particles, said chemical means being selected from the group consisting of polyalkylene amines and their lower alkyl ammonium salts, aminodextrans, chitosan, protamine, positively charged liposomes, polylysine, heparin, dextran sulfate, negatively charged phospholipid vesicles and polycarboxylic acids.

2. The method of claim 1 wherein said non-specific coupling is reversible.

3. The method of claim 1 wherein said non-specific coupling results from charge interactions.

4. A method of separating suspended charged non-magnetic particles from a liquid medium, which comprises
combining in a liquid medium charged non-magnetic particles and like-charged magnetic particles, and chemical means for non-specifically binding said non-magnetic particles and said magnetic particles, said chemical means being selected from the group consisting of polyalkylene amines and their lower alkyl ammonium salts, aminodextrans, chitosan, protamine, positively charged liposomes, polylysine, heparin, dextran sulfate, negatively charged phospholipid vesicles and polycarboxylic acids, and subjecting said medium to a magnetic field gradient to separate said bound particles from said medium.

5. The method of claim 4 wherein said non-specific binding is the result of charge interactions.

6. The method of claim 4 wherein said magnetic particles have a diameter of from about 5 to 100 nm.

7. The method of claim 4 wherein said non-magnetic particles are biological particles.

8. The method of claim 7 wherein said biological particles are selected from the group consisting of cells and microorganisms.

9. The method of claim 4 wherein said non-magnetic particles are erythrocytes.

10. The method of claim 4 wherein said non-magnetic particles are synthetic particles.

11. The method of claim 10 wherein said non-magnetic particles are selected from the group consisting of liposomes and latex particles.

12. The method of claim 4 wherein a member of a specific binding pair is bound to said non-magnetic particles.

13. The method of claim 4 wherein said bound non-magnetic particles are treated with a reagent to reverse their binding to said magnetic particles.

14. The method of claim 13 wherein said reagent to reverse said binding is a high ionic strength solution.

15. The method of claim 13 wherein said polyalkylene amine and ammonium salts thereof are selected from the group consisting of polyethyleneimine, polypropyleneimine and polybrene.

16. The method of claim 15 wherein said polycarboxylic acids are selected from the group consisting of polyacrylate and polyglutamates.

17. The method of claim 4 wherein said chemical means is selected from the group consisting of polybrene and polyethyleneimine.

18. The method of claim 4 wherein said non-magnetic particles are liposomes and after separation said bound non-magnetic particles are combined with a detergent.

19. The method of claim 4 wherein said magnetic particles are present in a magnetic fluid prior to combination with said non magnetic particles.

20. The method of claim 4 wherein said magnetic particles are coated with a protein.

21. A method for removing cells from whole blood, which comprises combining in a liquid medium a whole blood sample and negatively charged magnetic particles and chemical means for non-specific binding said magnetic particles to said cells, said chemical means being selected from the group consisting of polyalkylene amines and their lower alkyl ammonium salts, aminodextrans, chitosan, protamine, positively charged liposomes, polylysine, heparin, dextran sulfate, negatively charged phospholipid vesicles and polycarboxylic acids, and subjecting said medium to a magnetic field gradient to separate said bound cells from said medium.

22. The method of claim 21 wherein said chemical means is selected from a group consisting of polybrene, polyalkyleneimine, aminodextran, chitosan, and positively charged liposomes.

23. The method of claim 21 wherein said chemical means is polybrene or polyethyleneimine.

24. The method of claim 21 wherein said magnetic particles are from about 5–100 nm in diameter.

25. The method of claim 21 wherein said magnetic particles are present in a ferrofluid prior to combination with said blood sample.

26. The method of claim 25 wherein said magnetic particles are coated with a protein.

* * * * *